(12) United States Patent
Haindl

(10) Patent No.: US 9,987,040 B2
(45) Date of Patent: Jun. 5, 2018

(54) SUPRAPUBIC SAFETY CANNULA

(76) Inventor: Hans Haindl, Wennigsen (DE)

(*) Notice: Subject to any disclaimer, the term of this patent is extended or adjusted under 35 U.S.C. 154(b) by 772 days.

(21) Appl. No.: 13/982,021

(22) PCT Filed: Jan. 23, 2012

(86) PCT No.: PCT/EP2012/050966
§ 371 (c)(1),
(2), (4) Date: Oct. 14, 2013

(87) PCT Pub. No.: WO2012/101089
PCT Pub. Date: Aug. 2, 2012

(65) Prior Publication Data
US 2014/0052166 A1    Feb. 20, 2014

(30) Foreign Application Priority Data

Jan. 26, 2011 (DE) .................. 10 2011 009 482

(51) Int. Cl.
*A61B 17/34*   (2006.01)
*A61M 25/06*   (2006.01)
*A61M 25/01*   (2006.01)

(52) U.S. Cl.
CPC ...... *A61B 17/3415* (2013.01); *A61B 17/3421* (2013.01); *A61M 25/065* (2013.01);
(Continued)

(58) Field of Classification Search
CPC ............ A61M 25/0606; A61M 25/065; A61M 2025/0191; A61B 17/3415; A61B 17/3421; A61B 17/3468
See application file for complete search history.

(56) References Cited

U.S. PATENT DOCUMENTS 3,545,443 A  *  12/1970  Ansari ................ A61M 25/065
                                                        604/160
7,708,721 B2    5/2010  Khaw
(Continued)

FOREIGN PATENT DOCUMENTS

DE    2 104 211    12/1971
DE    33 47 150    7/1985
(Continued)

OTHER PUBLICATIONS

International Report on Patentability including Notification of Transmittal for PCT Application No. PCT/EP2012/050966, dated Jul. 30, 2013, 2 pages.
(Continued)

*Primary Examiner* — Elizabeth Houston
*Assistant Examiner* — Tin Nguyen
(74) *Attorney, Agent, or Firm* — Westman, Champlin & Koehler, P.A.

(57) ABSTRACT

The present invention relates to a cannula for puncturing body cavities, comprising an inner and an outer longitudinally cut sleeve with proximal and distal ends. The inner sleeve is arranged within the outer sleeve so as to be longitudinally displaceable and rotatable within the outer sleeve such that the longitudinal cut of the inner sleeve is covered by the outer sleeve in a first rotational position and the longitudinal cuts of the inner and outer sleeves are placed on top of each other in a second rotational position. The distal end of the inner sleeve is provided with a puncture tip that is completely retracted into the outer sleeve if the inner sleeve is in the second rotational position, wherein the inner and outer sleeves and/or the two handle portions are, preferably unreleasably, locked to one another.

12 Claims, 24 Drawing Sheets

(52) U.S. Cl.
CPC ..... *A61M 25/0606* (2013.01); *A61B 17/3468* (2013.01); *A61M 2025/0191* (2013.01)

(56) References Cited

U.S. PATENT DOCUMENTS

2005/0090852 A1* 4/2005 Layne ................ A61B 17/3417
606/190
2007/0276288 A1* 11/2007 Khaw ................... A61M 25/01
600/566

FOREIGN PATENT DOCUMENTS

| | | |
|---|---|---|
| DE | 41 03 977 | 8/1992 |
| DE | 43 16 793 | 9/1994 |
| DE | 10 2005 015 556 | 10/2006 |
| DE | 698 37 667 | 1/2008 |
| EP | 0 499 147 | 8/1992 |
| FR | 2 129 116 | 10/1972 |
| JP | 60-158870 A | 8/1985 |
| JP | 2001-238947 A | 9/2001 |

OTHER PUBLICATIONS

Translation of Written Opinion for PCT Application No. PCT/EP2012/050966, dated Jul. 3, 2013, 5 pages.
Office Action for Japanese Patent Application No. 2013-550848, dated Sep. 14, 2015, 4 pages.
International Search Report for PCT Application No. PCT/EP2012/050966, dated Jul. 3, 2012, 4 pages.

\* cited by examiner

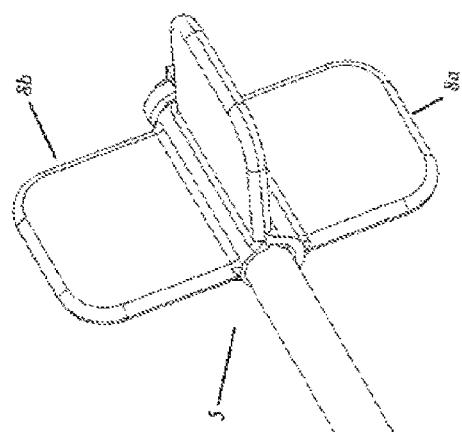
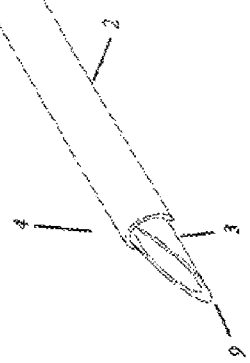
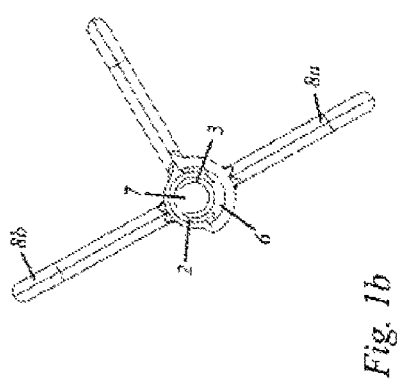

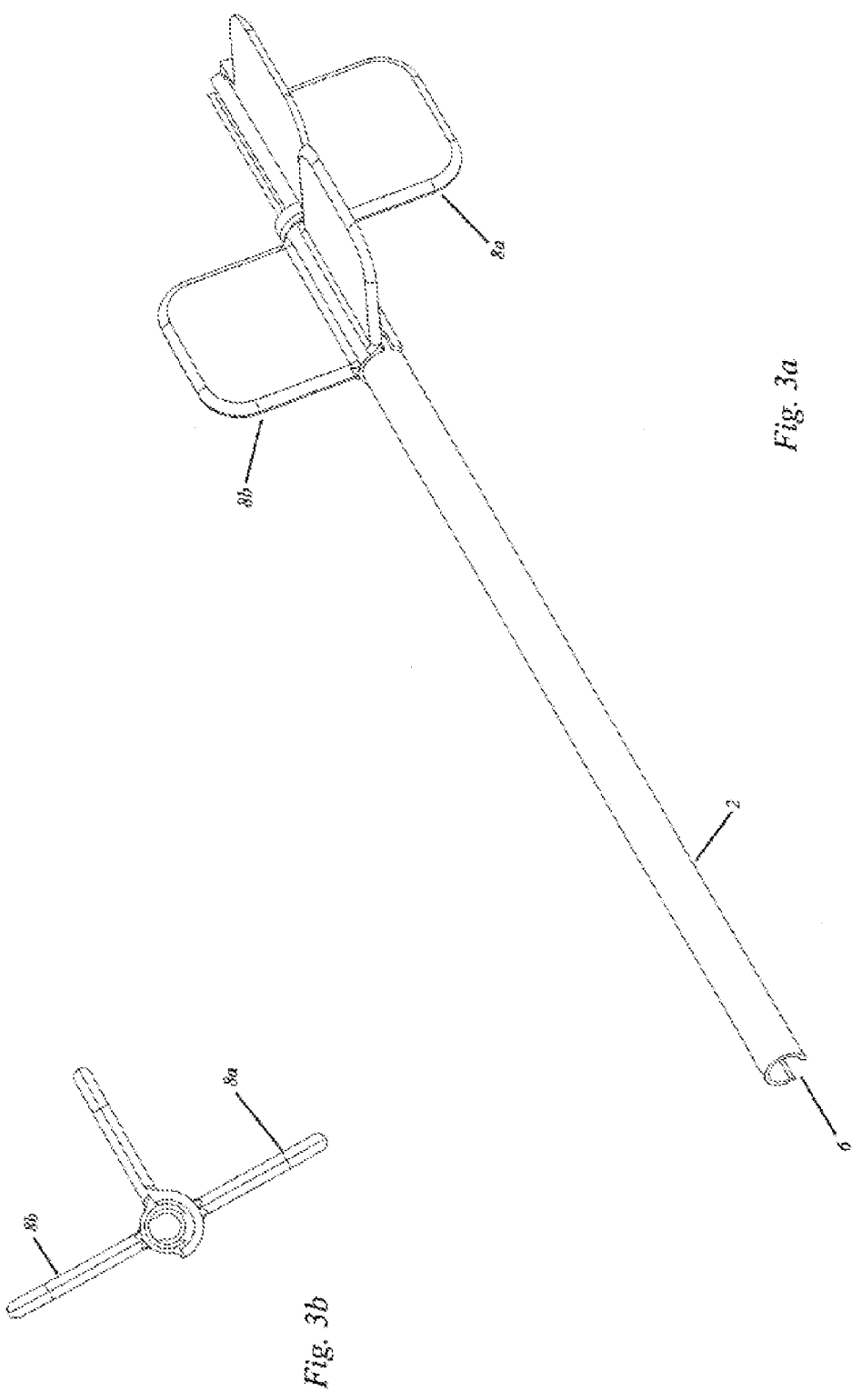

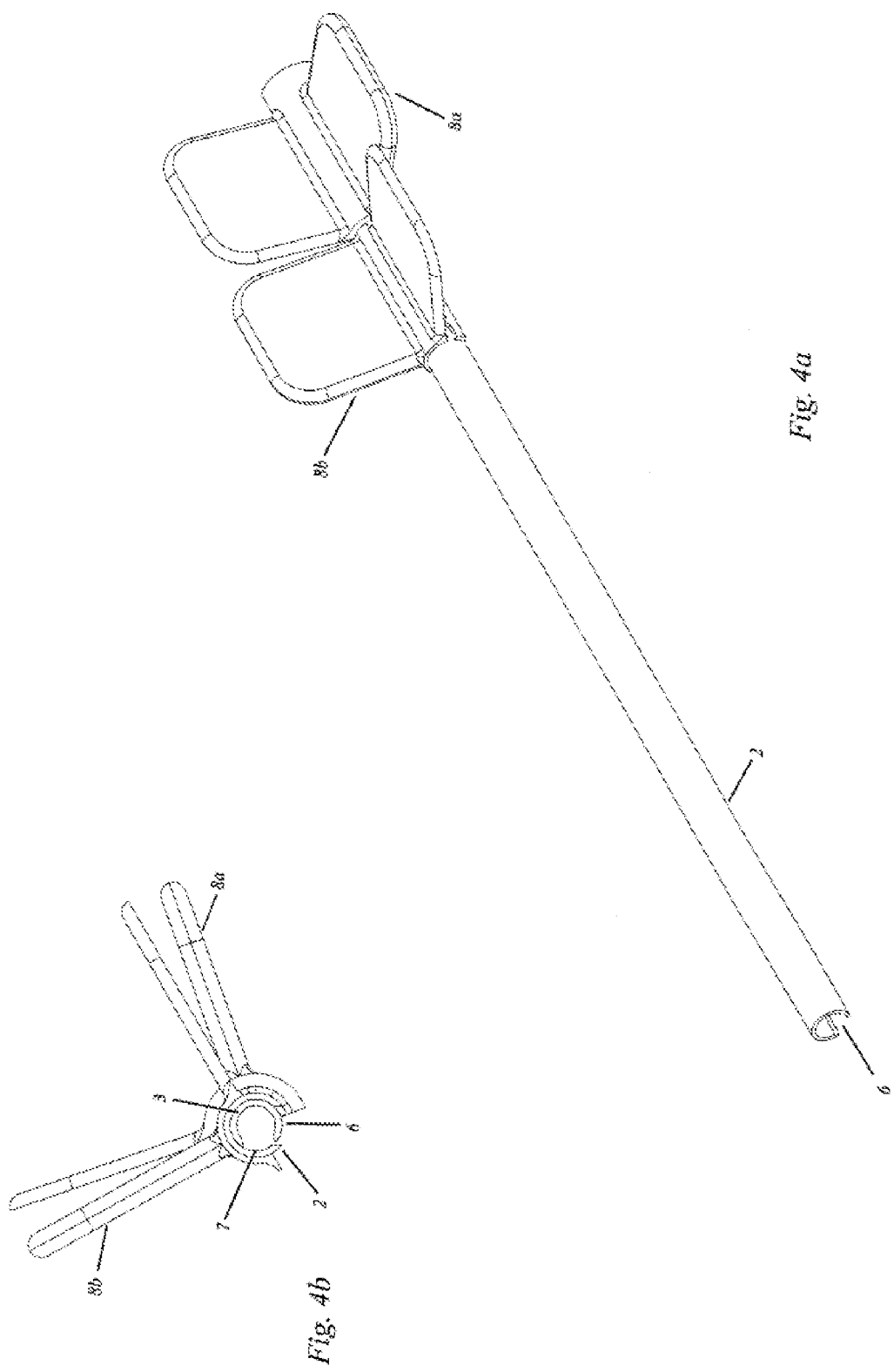

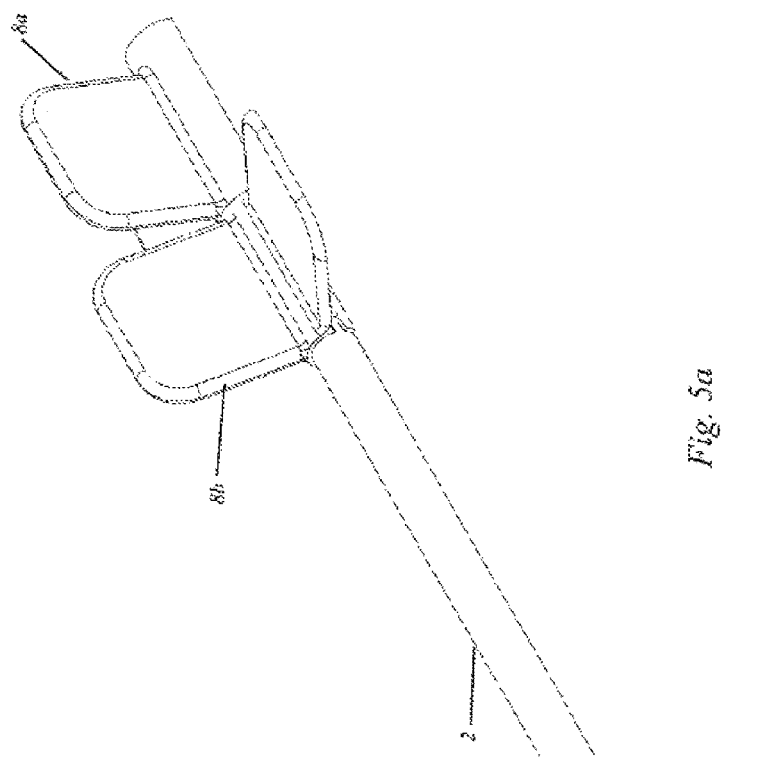
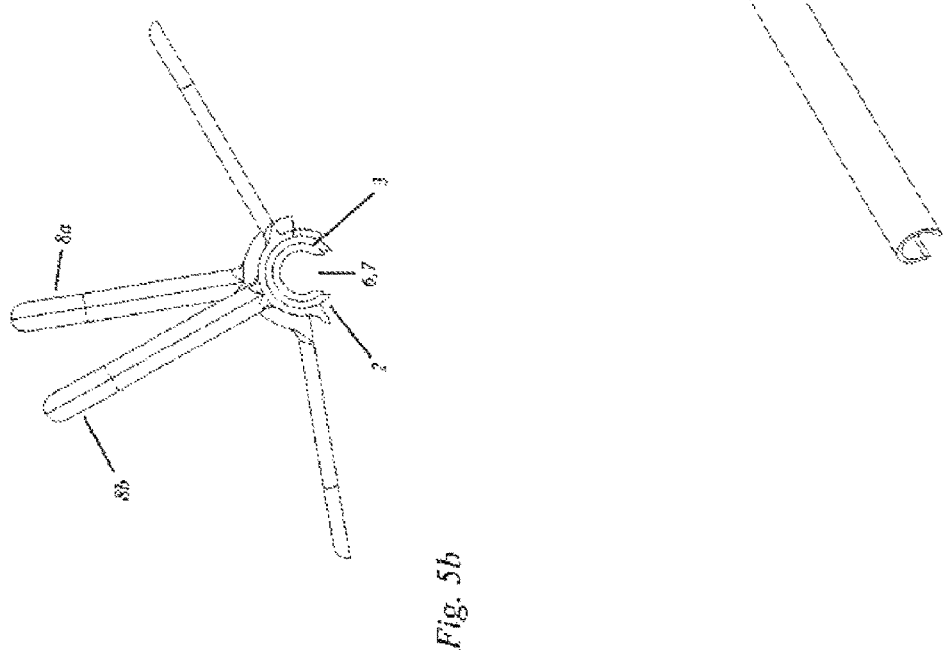
Fig. 5a
Fig. 5b

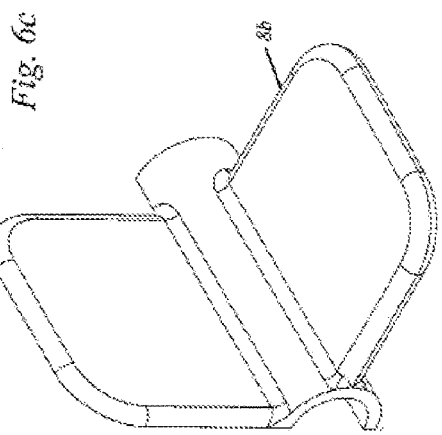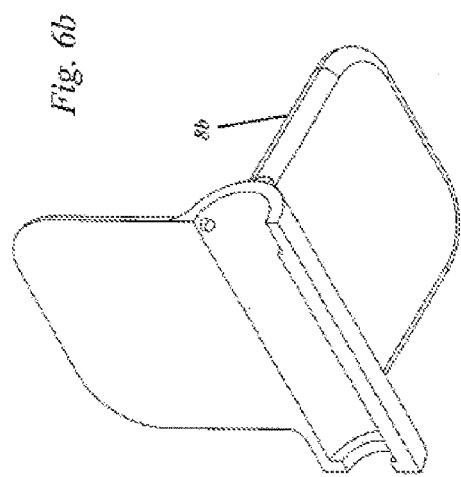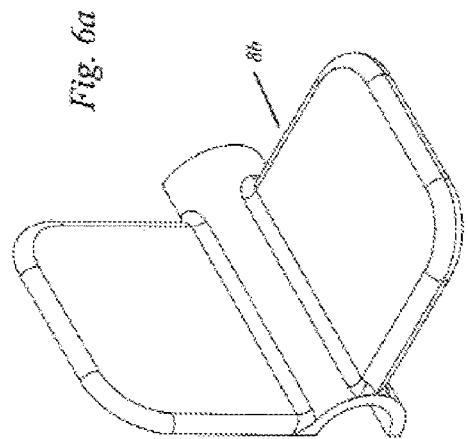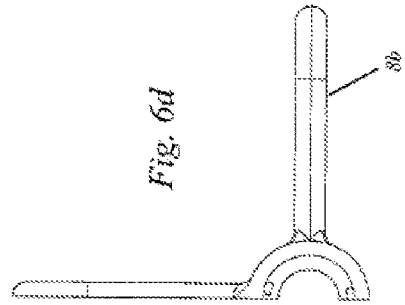

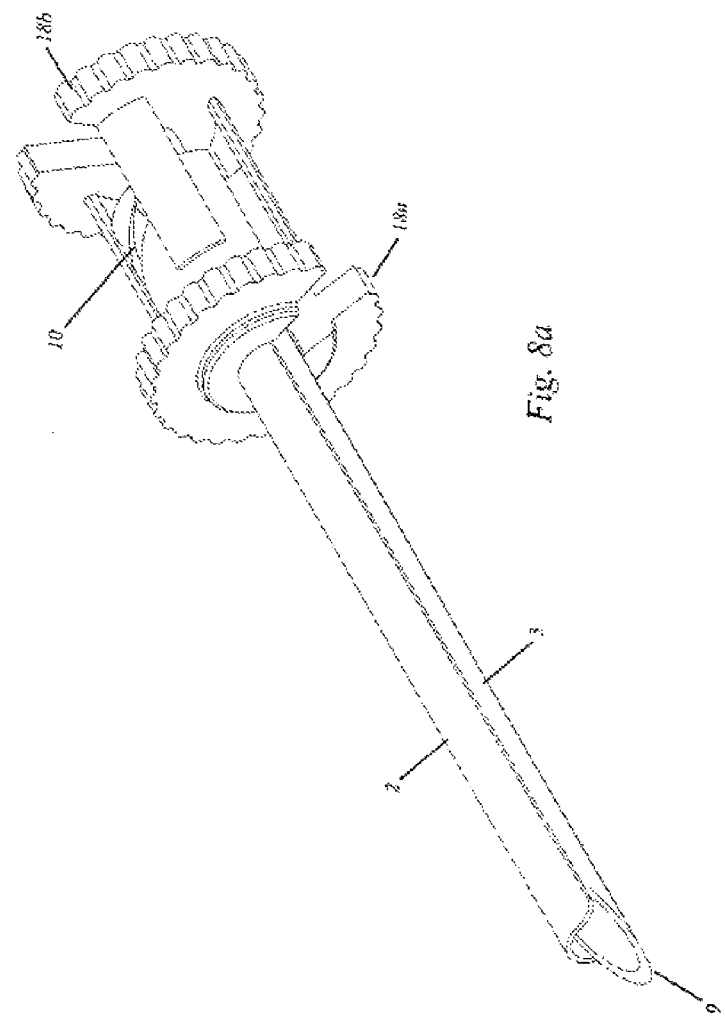
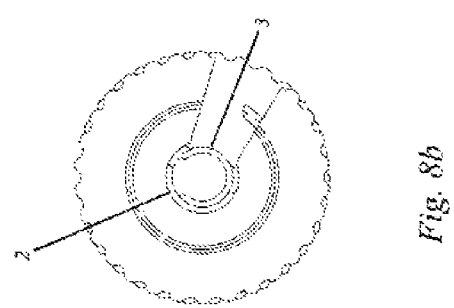

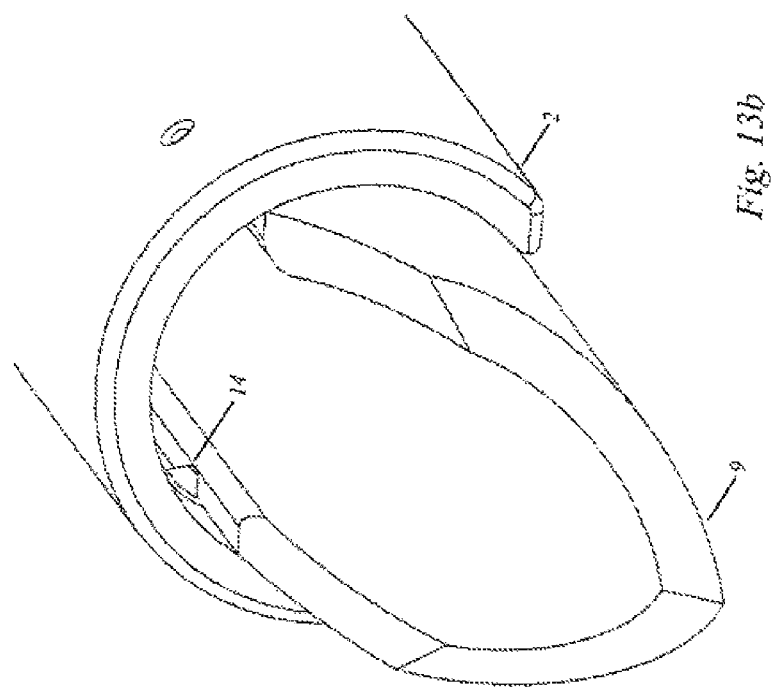
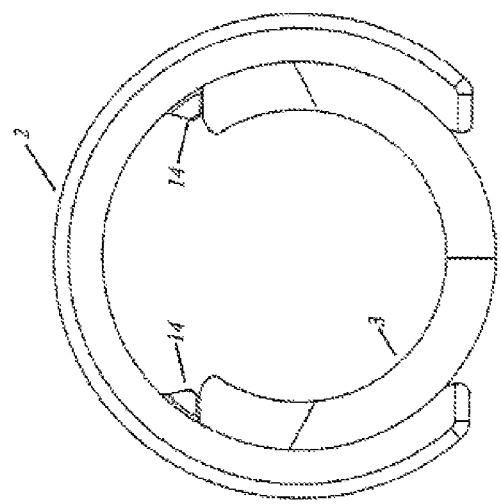
Fig. 13a
Fig. 13b

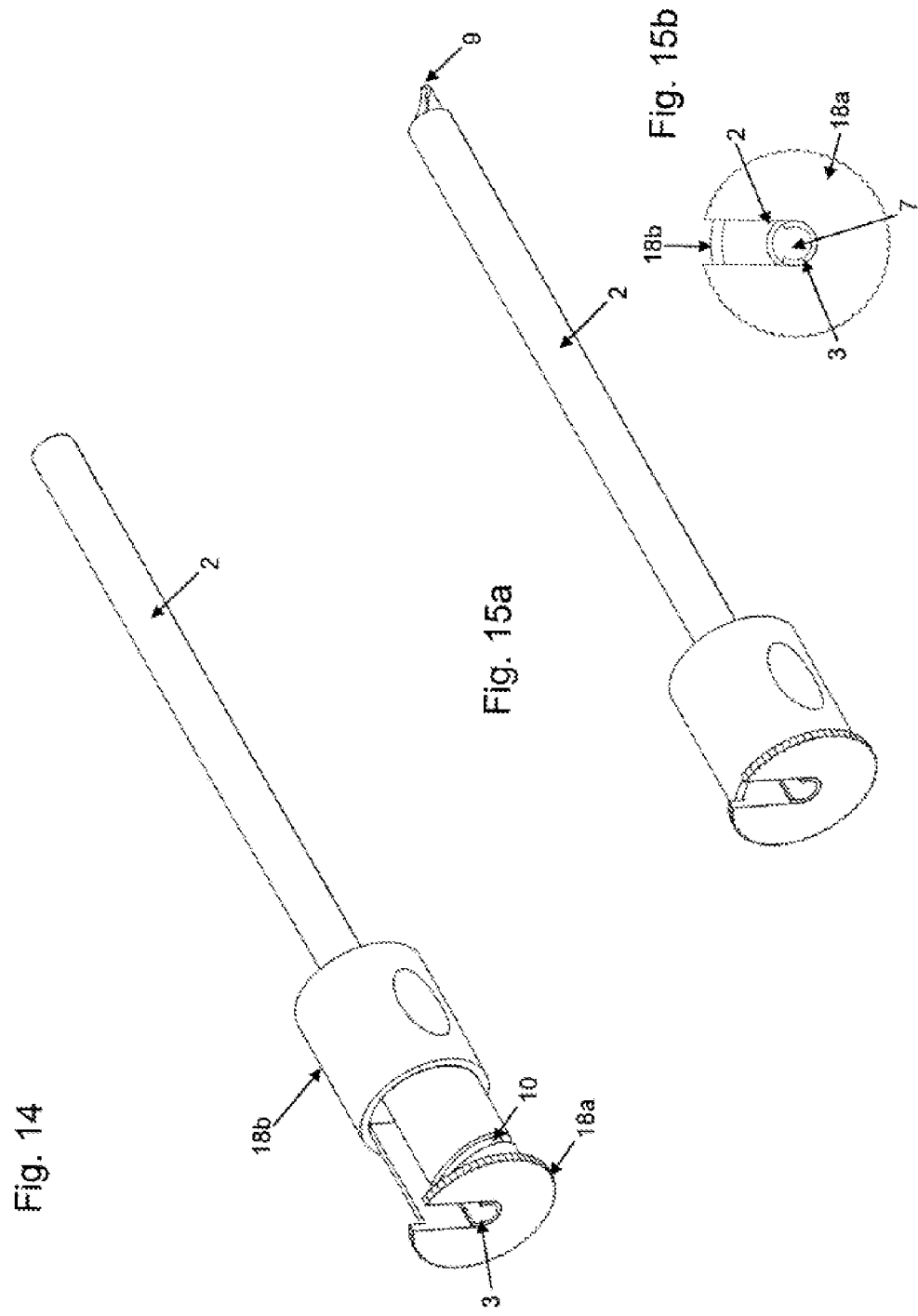

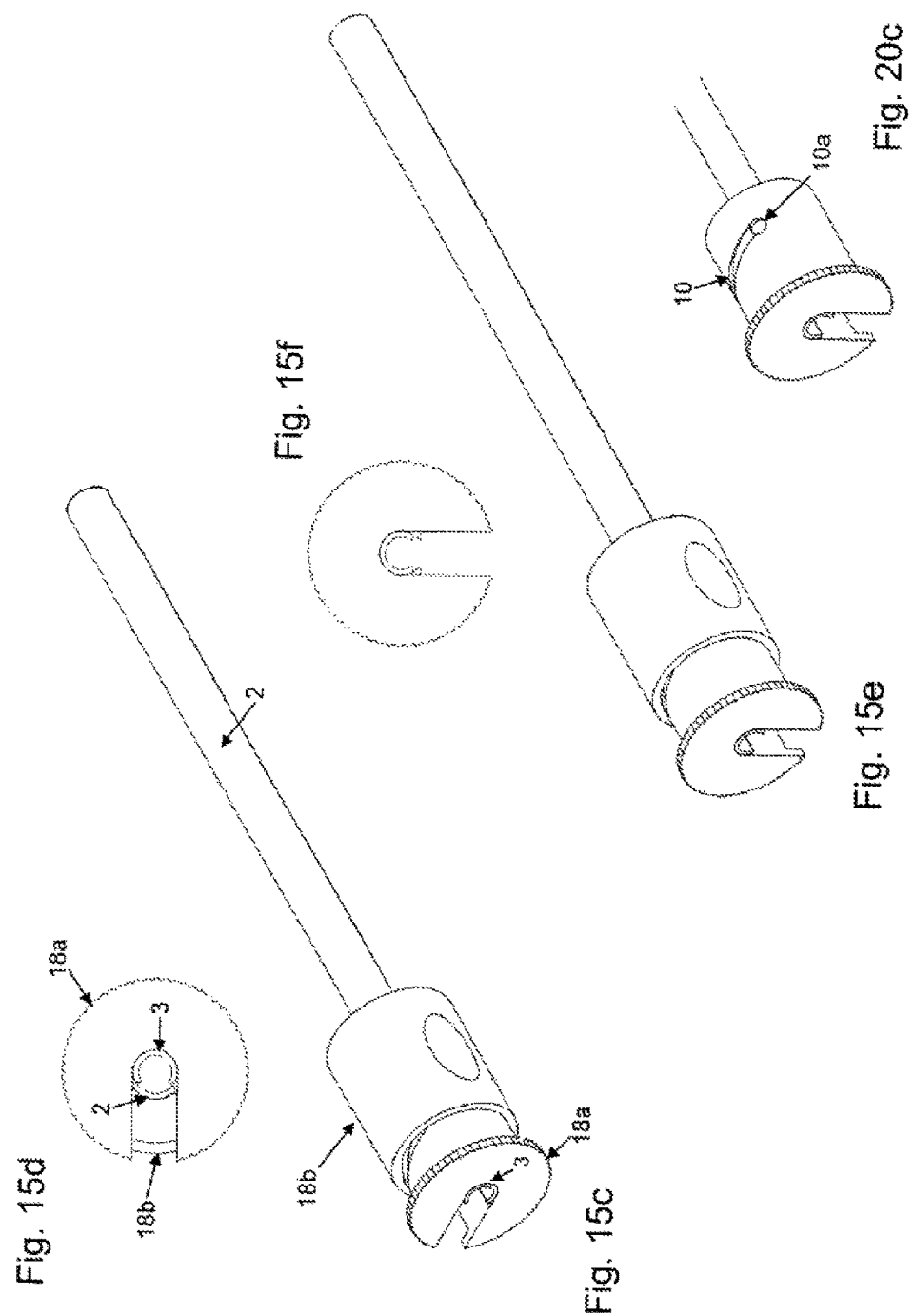

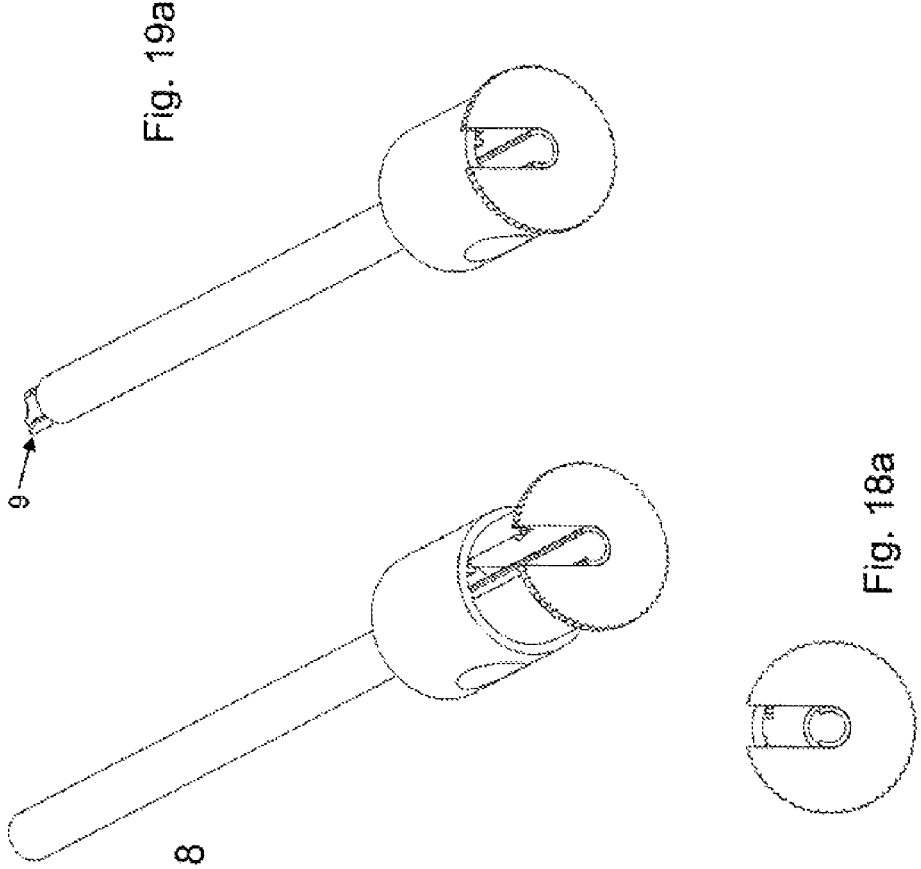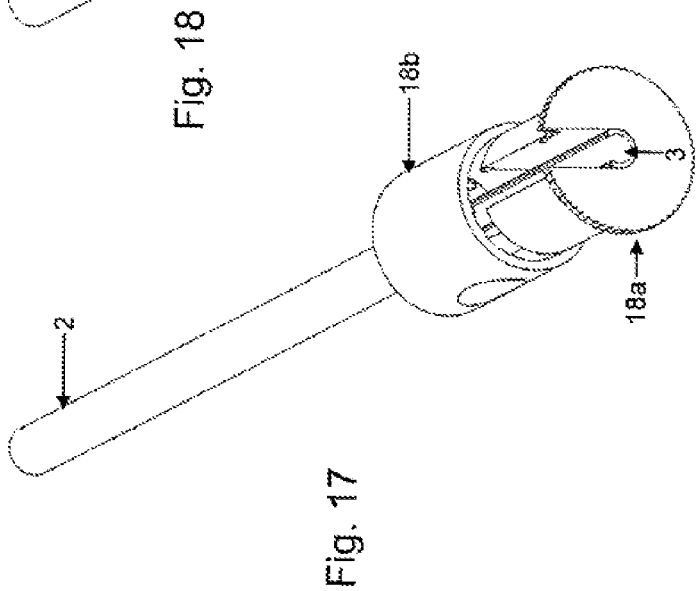

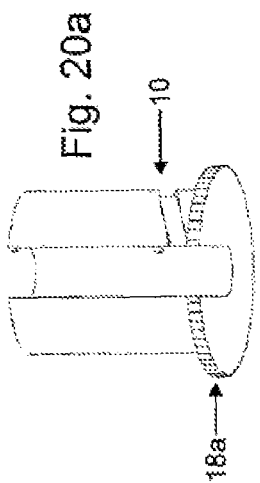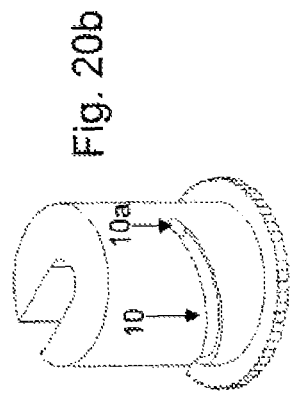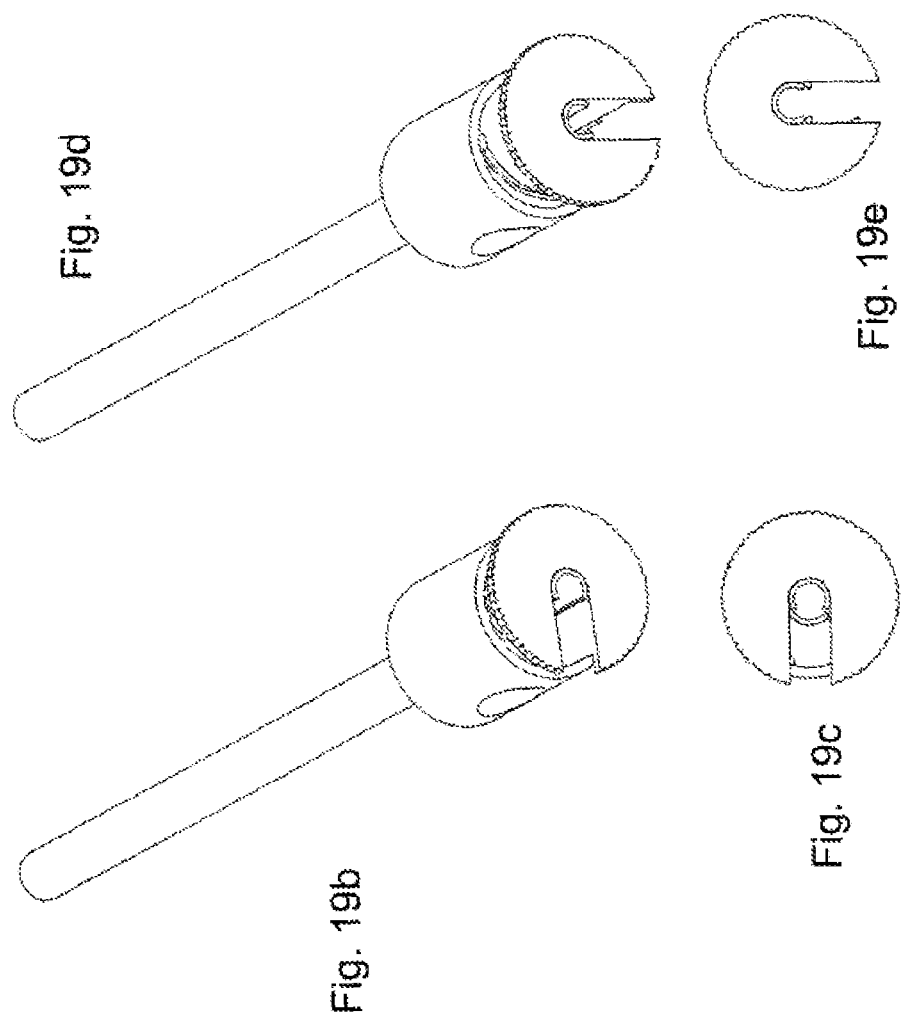

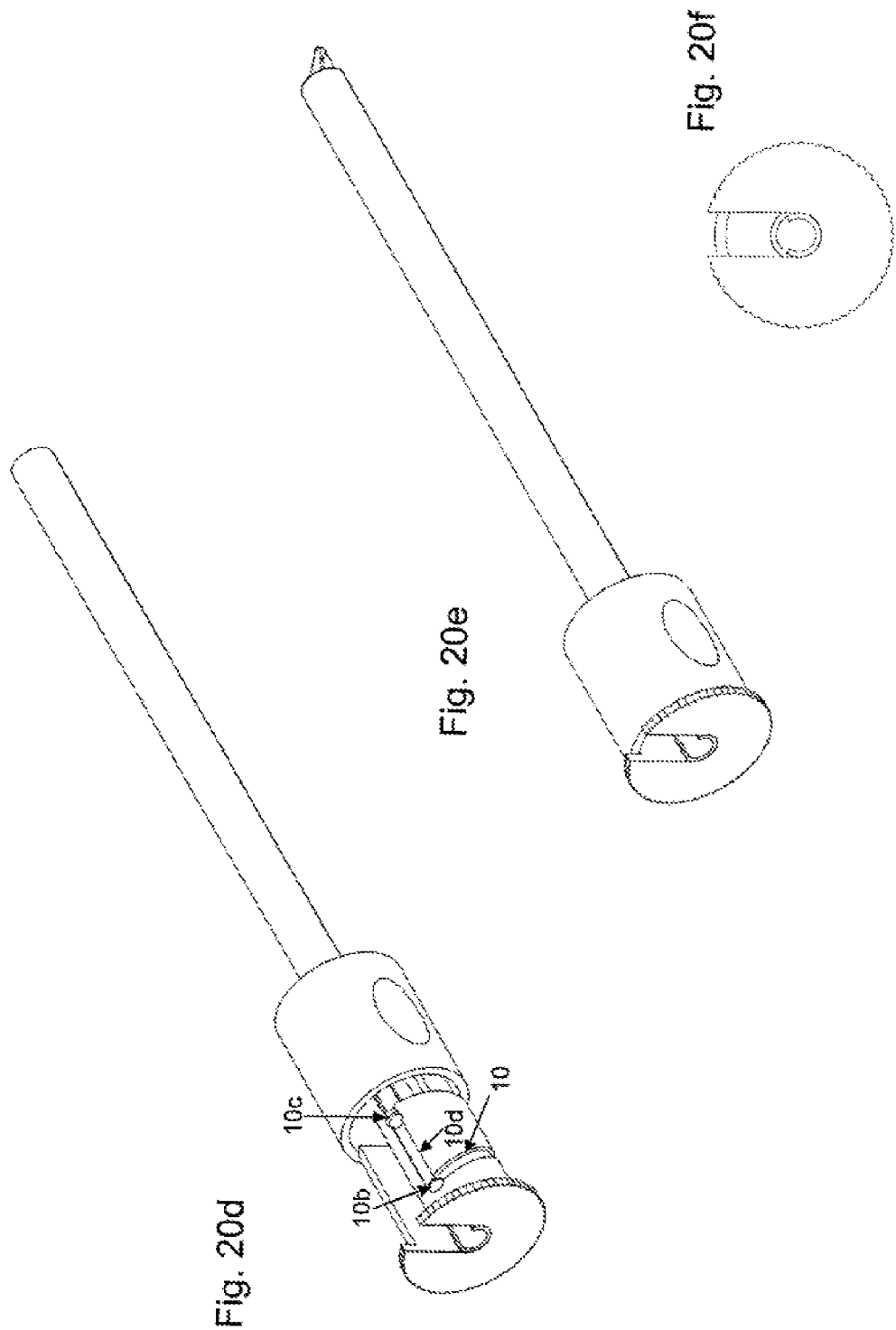

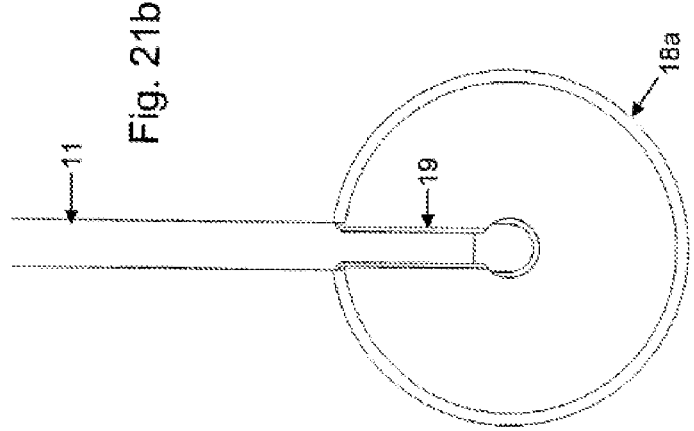
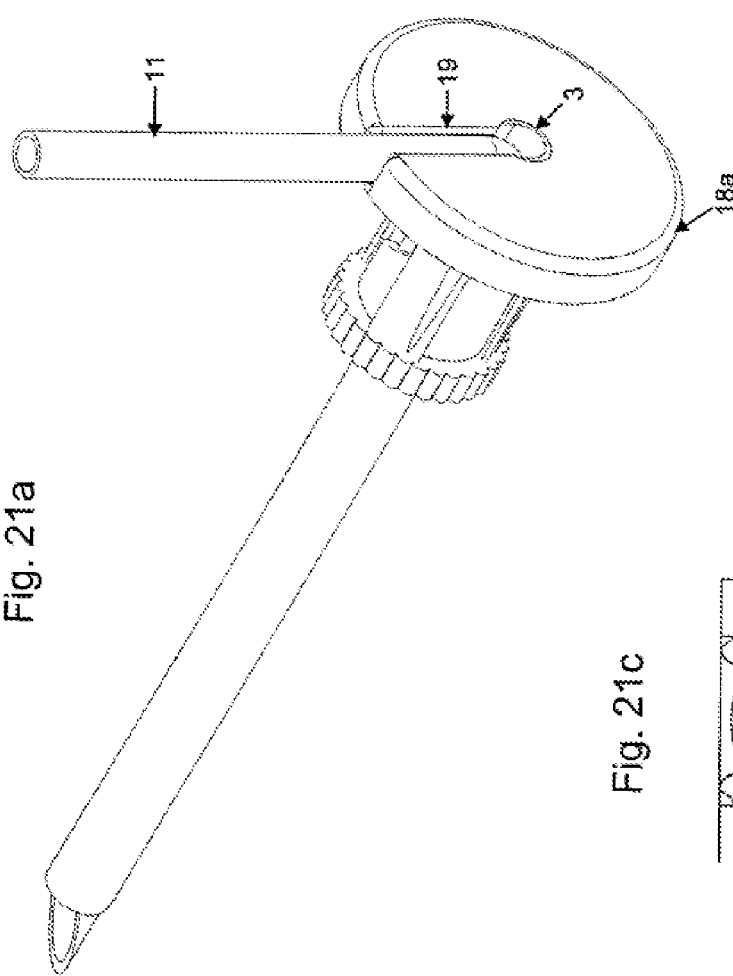
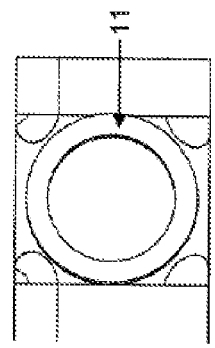

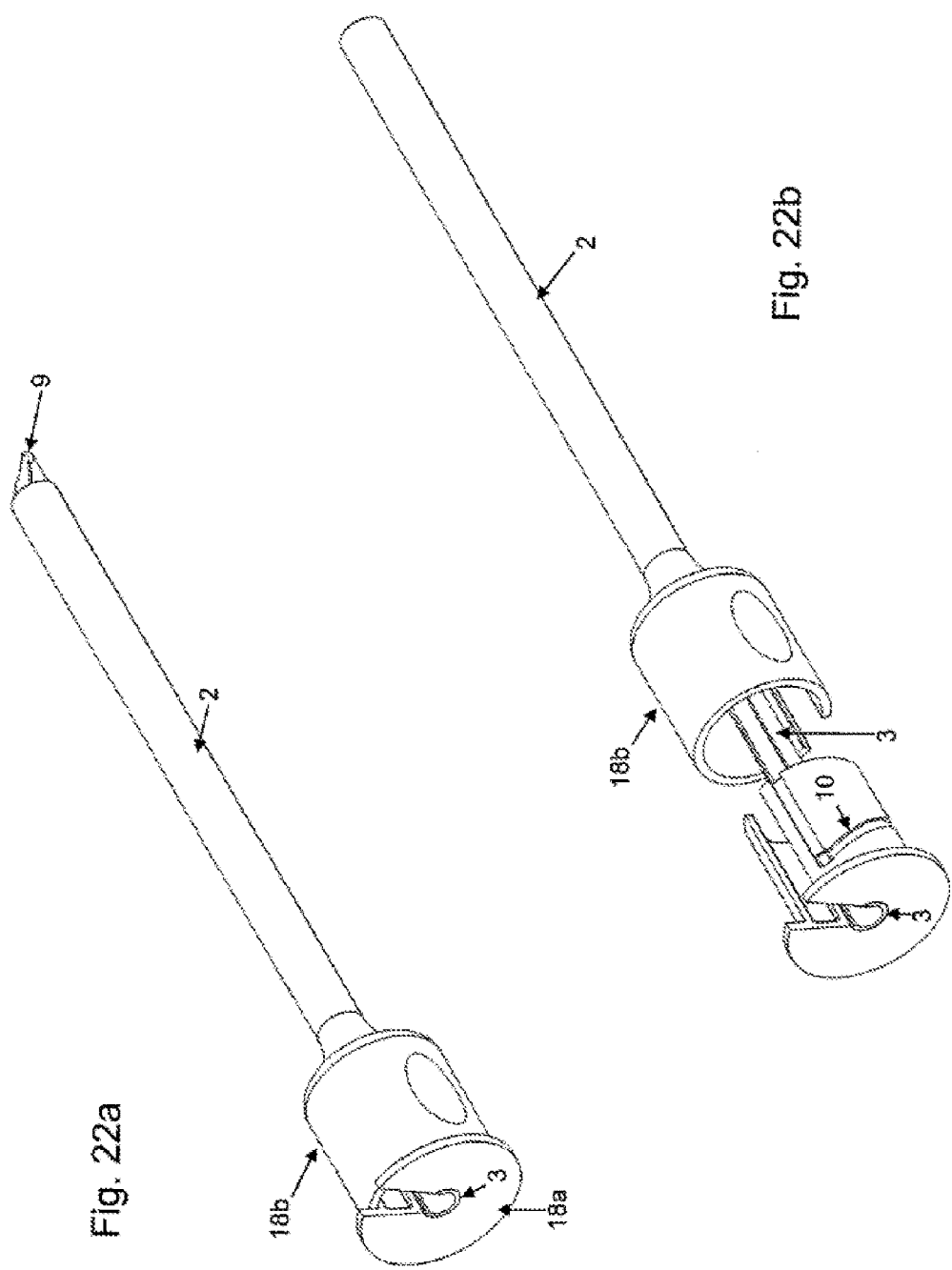

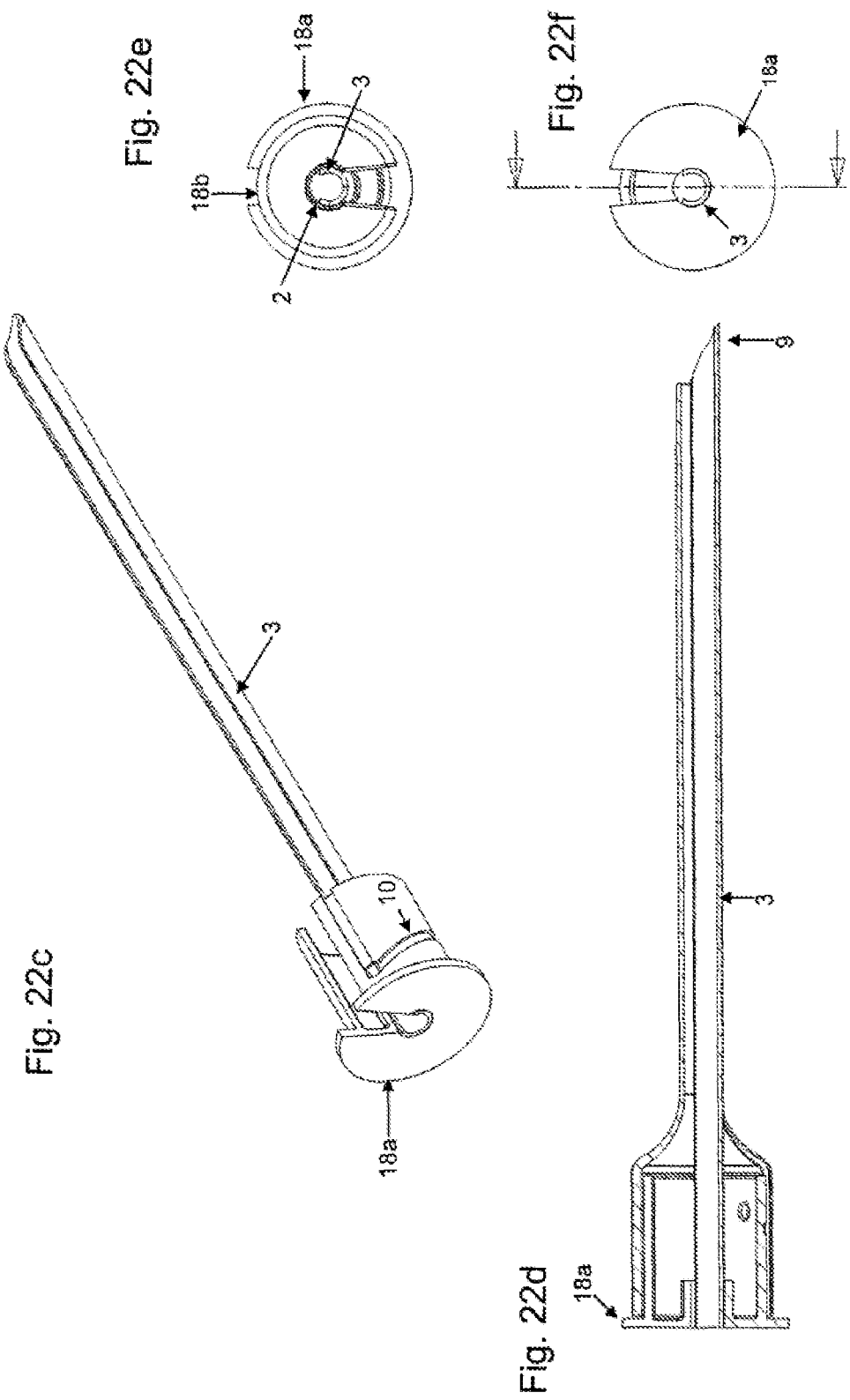

SUPRAPUBIC SAFETY CANNULA

CROSS-REFERENCE TO RELATED APPLICATION

This Application is a Section 371 National Stage Application of International Application No. PCT/EP2012/050966, filed 23 Jan. 2012 and published as WO 2012/101089 A1 on 2 Aug. 2012, in German, the contents of which are hereby incorporated by reference in their entirety.

The present invention relates to a safety cannula, in particular a safety cannula for puncturing body cavities, e.g. a suprapubic safety cannula.

Different fields of medicine are facing the problem that upon insertion of a catheter into a body cavity through a cannula, the removal of the cannula via the permanently connected catheter neck is no longer possible. Different solutions to this problem are known in the art. For example in central venous catheters, protective plastic bags have been attached over the cannula so as to prevent the catheter from damage and the patient or operator from injury.

The aforementioned problem is also known in the field of urology. Suprapubic puncturing of the bladder (i.e. through the abdominal wall) has become an accepted method for enabling lasting urinary diversion. To this end, so-called suprapubic catheters are used, which involve lower infection rates than catheters that are inserted through the urethra. The problem that the cannula can no longer be removed via the catheter neck once the catheter has been inserted and the cannula has been removed again from the catheter also occurs with suprapubic catheters. However, the cannula cannot remain on the catheter since it could easily damage the catheter and/or injure the patient.

Splitting the cannula upon use is known to enable a removal of the cannula from the catheter. The operator, e.g., pulls at two handles in opposite directions so as to split the cannula longitudinally into two. The two halves of the cannula can then simply be removed from the catheter. Such cannulae are for example known from DE 43 16 793 C1, DE 2 104 211 C1, DE 698 37 667 T2 and DE 10 2005 015 556 A1. Examples of splittable cannulae are rolled cannulae, which have an open gap on one side and are weakened on the other side, cannulae that are mechanically weakened on two sides and laser-perforated cannulae.

However, the splitting process requires extreme forces and involves a high risk of injury for the operator. The splitting edges of the cannulae are often covered with sharp ridges that may cause cutting damage upon touch.

A known prior art alternative that does not require cannula splitting is the so-called trough cannula from which the catheter can be removed laterally. Examples of such trough cannulae are disclosed in EP 0 499 147 B1 and DE 41 03 977 A1. U.S. Pat. No. 3,545,443 as well as DE 33 47 150 A1 disclose cannulae consisting of two longitudinally cut, overlapping sleeves.

U.S. Pat. No. 7,708,721 B2 discloses a cannula having inner and outer sheaths that are slidable against each other. However, the tip of the cannula of the inner sheath cannot be locked in the withdrawn safety position so that the tip of the cannula cannot be prevented from exiting and causing injuries. Moreover, the thread described in U.S. Pat. No. 7,708,721 B2 is not technically feasible or only feasible with a disproportionate effort.

Even if the latter references reduce the risk of injury in that no split edges with sharp ridges are formed, the approaches suggested therein do not eliminate the danger of getting hurt and possibly infected by the extremely sharp puncture tip of the cannula. According to accident prevention regulation TRBA 250, hospital operators are obliged to provide their employees with cannula systems that do not involve a risk of injury. In the field of urology, for example, no system without risk of injury is so far available for suprapubic bladder puncturing.

It is therefore an object of the present invention to provide a safety cannula, in particular a safety cannula for puncturing body cavities that further minimises the risk of injury and infection that known systems involve. This object is achieved by a cannula according to claim 1.

The present invention provides for a cannula for puncturing body cavities comprising an outer and an inner longitudinally cut sleeve each having proximal and distal ends. The inner sleeve is arranged inside the outer sleeve and is longitudinally displaceable within the outer sleeve. Moreover, the inner sleeve and the outer sleeve can be rotated against each other such that the longitudinal cut of the inner sleeve is completely covered by the outer sleeve in a first rotational position, while the longitudinal cuts of the inner and the outer sleeve are placed on top of each other in a second rotational position. In a first rotational position, the two sleeves form a completely closed cannula that is suitable for puncturing body cavities. In the second position, the two longitudinal cuts of the sleeves are arranged so as to be aligned so that a catheter or catheter tube within the inner sleeve can be removed from the sleeve through these longitudinal cuts. The invention is based on the idea that only the inner sleeve comprises a sharpened puncture tip, whereas the distal end of the outer sleeve is configured such that it cannot cause injuries and that this sharpened puncture tip of the inner sleeve is completely protected by the outer sleeve when the cannula is removed from the catheter or catheter tube. Therefore, the inner sleeve of the invention is provided at its distal end with a puncture tip that is completely retractable or retracted into the outer sleeve, when the inner sleeve is in the second rotational position.

Thus, it is made sure that the sharp puncture tip is no longer accessible to the operator or the hospital staff when the cannula is removed from the catheter or catheter tub. Therefore, injuries and possible infections by the puncture tip are effectively avoided. According to the invention, two preferred embodiments of this safety mechanism are disclosed.

According to a first preferred embodiment, the inner sleeve can only be rotated into the second position if the puncture tip of the inner sleeve has already been completely retracted into the outer sleeve. Consequently, the cannula can be opened by a two-step movement: First, the inner sleeve has to be retracted within the outer sleeve to such an extent that the puncture tip of the inner sleeve is completely covered or protected by the outer sleeve. Only in this position does the cannula according to the invention permit a rotation of the two sleeves against one another into the second position, in which the longitudinal cuts of the two sleeves are placed on top of each other. Preferably, the two movements are made by means of handles or the like, which first have to be longitudinally moved against each other, whereupon they can be rotated against one another.

Therefore, the cannula is preferably provided at its proximal end with two handle portions or wings that prevent the inner sleeve from rotating as long as the puncture tip of the inner sleeve distally extends from the outer sleeve. Preferably, a first handle portion or wing is connected to the inner sleeve and a second handle portion or wing to the outer sleeve.

According to a second preferred embodiment, the puncture tip of the inner sleeve is completely retracted into the outer sleeve when the inner sleeve is rotated into the second position. In other words, in this embodiment, the two movements, i.e. the longitudinal shifting on the one hand and the rotation of the sleeves against each other, on the other hand, are coupled so that a rotation of the sleeves against each other simultaneously effects a longitudinal shifting of the sleeves and vice versa. Preferably, the rotation and the shifting of the sleeves are coupled by a thread of sufficient pitch; however, other coupling options are also applicable according to the invention. The thread is preferably provided at the handle portions or other proximal portions having a larger diameter than the cannula. Thus, threading is simpler and less expensive than if the inner and outer surface of the cannula had to be threaded.

Preferably, the sleeves are rotated against each other by means of handle portions or wings attached thereon. Thus, the proximal end of the cannula is preferably provided with a first handle portion connected to the inner sleeve and a second handle portion connected to the outer sleeve. A rotational movement of the handle portions relative to each other causes a complete retraction of the puncture tip of the inner sleeve into the outer sleeve and the placement of the longitudinal cuts of the inner and outer sleeves on top of each other.

In case of both embodiments, the distal ends of the outer sleeve are preferably essentially blunt. In particular, the distal end of the outer sleeve is configured such that injuries at the outer sleeve are avoided.

Moreover, the inner and the outer sleeves and/or the two handle portions are interlocked in the second position. This is to avoid that the two sleeves turn back or shift with respect to one another when the cannula is removed from the catheter (or later), which would expose the puncture tip of the inner sleeve. Preferably, the engagement is non-detachable so that the cannula may only be used as a disposable cannula.

It is moreover preferred that the inner sleeve is prevented from completely turning back from the second position into the first position. This can for example be achieved in that the inner sleeve (which may be slightly prestressed) expands in the second position so that turning back into the first position is made impossible since, if expanded, the inner sleeve can no longer be accommodated by the outer sleeve.

Moreover, the distal end of the inner surface of the outer sleeve is preferably provided with two or more stabilising elements that stabilise the inner sleeve during puncturing against any compressive or torsional forces. The stabilising elements may be notches, seams or projections at the inner surface of the outer sleeve.

According to a further preferred embodiment, a third rotational position is provided between the first and the second rotational position. In this third rotational position, the puncture tip is already completely retractable or has been completely retracted, while the longitudinal cuts of the inner and the outer sleeve are not yet placed on top of each other. Preferably, the inner sleeve is prevented from completely turning back from the third position into the first position.

All features described with reference to the second position may additionally or alternatively be also provided for the third position. A rotation of the inner sleeve into the third position can, for example, lead to a complete retraction of the puncture tip of the inner sleeve into the outer sleeve.

Preferably, the rotational movement and the shifting movement of the sleeves are coupled by a thread. At its proximal end, the cannula is preferably provided with a first handle portion connected to the inner sleeve and a second handle portion connected to the outer sleeve. A rotational movement of the handle portions relative to each other first causes a complete retraction of the puncture tip into the outer sleeve in the third rotational position, whereupon the longitudinal cuts of the inner and the outer sleeve a placed on top of each other in the second rotational position. The thread is preferably provided at the handle portions or other proximal portions having a larger diameter than the cannula. Threading is thus simpler and less expensive than if the inside and outside of the cannula has to be threaded.

It is moreover preferred that the outer sleeve and the handle portion connected thereto are made of plastics and preferably of one piece. It is i.a. particularly simple to make the thread structure in the handle portions of plastics.

According to a preferred embodiment, the handle portion connected to the inner sleeve is provided with a pressure plate. This pressure plate enables the operator to exert pressure, e.g., by means of his/her palm or thumb over a large surface area during puncturing. This makes puncturing more easy for the operator and thus the operation safe. Since the inner sleeve should be capable of receiving any catheter or the like, the pressure plate is preferably provided with a slot or a guide for a catheter so that during puncturing the catheter can, e.g., be prevented from getting stuck or wedged between the pressure plate and palm or thumb.

The present invention moreover relates to a kit comprising the cannula described above and a catheter that can be accommodated within the inner sleeve of the cannula, wherein the catheter can be removed from the cannula in the second cannula position by means of the longitudinal cuts of the sleeves placed on top of each other. To this end, the dimensions of the longitudinal cuts of the sleeves should preferably be adapted to the diameter of the catheter. In case of a catheter of a relatively hard material, the longitudinal cuts should preferably be at least as large as the diameter of the catheter. If, however, the catheter material is relatively soft, the catheter can also be removed via slots that are smaller than the catheter diameter, taking advantage of the elasticity of the catheter.

Although the description exemplarily refers to a suprapubic cannula, the subject-matter of the invention is not restricted in any way thereto. It is clear to the skilled person that all the safety features described herein are also applicable to any other cannulae, in particular puncture cannulae.

Preferred embodiments of the present invention will be described in the following with reference to the drawings, in which:

FIGS. 1a, 2a, 3a, 4a and 5a show (a) a perspective view and FIGS. 1b, 2b, 3b, 4b and 5b show a sectional view of a cannula according to a first embodiment of the invention with different positions of the inner and the outer sleeve relative to each other;

FIGS. 6a-6f show a detailed view of the embodiment of FIGS. 1-5 with different positions of the inner sleeve and the outer sleeve relative to each other;

FIGS. 7a, 8a, 9a and 10a show a perspective view and FIGS. 7b, 8b, 9b and 10b show a sectional view of a cannula according to a second embodiment of the invention;

FIG. 13a shows a sectional view and FIG. 13b shows a perspective view of an inventive detail of a cannula tip according to the invention;

FIG. 14 shows a third embodiment of a cannula according to the invention;

FIGS. 15a-15f show the cannula according to FIG. 14 in the first (FIGS. 15a and 15b), the third (FIGS. 15c and 15d) and the second (FIGS. 15e and 15f) rotational position;

FIGS. 16a-16f show the cannula according to FIG. 14 in the first (FIGS. 16a and 16b), the third (FIGS. 16c and 16d) and the second (FIGS. 16e and 16f) rotational position;

FIG. 17 shows the cannula according to FIG. 14 before its mounting;

FIGS. 18-18a show the cannula according to FIG. 14 after mounting but before use;

FIGS. 19a-19e show the cannula according to FIG. 14 in the first (FIG. 19a), the third (FIGS. 19b and 19c) and the second (FIGS. 19d and 19e) rotational position;

FIGS. 20a-20c show the first handle portion of the cannula according to FIG. 14;

FIGS. 20d-20f show the cannula according to FIG. 14 in the position before mounting (FIG. 20d) and in the first rotational position (FIGS. 20e and 20f);

FIGS. 21a-21c show a fourth embodiment of the cannula according to the invention; and FIGS. 22a-22f show a fifth embodiment of the cannula according to the invention.

Figure 2A:
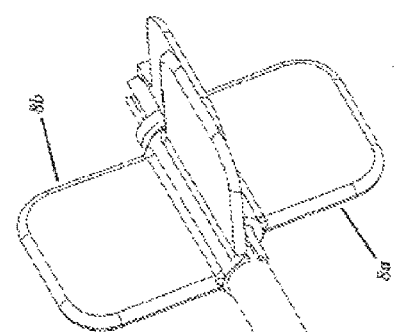
Figure 2B:
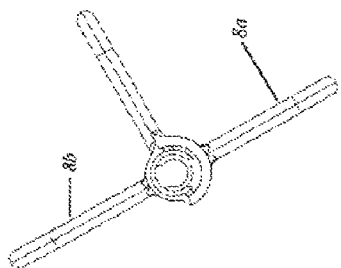
Figure 6F:
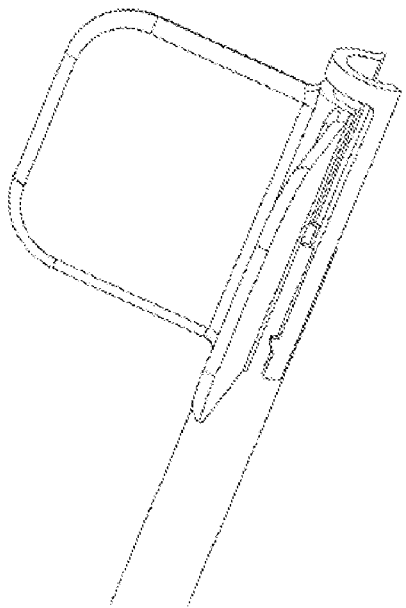
Figure 6E:
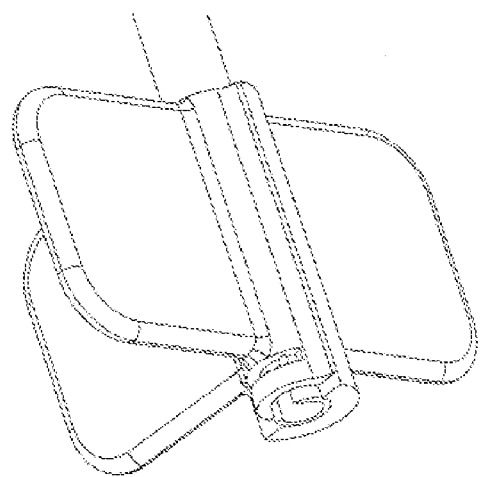

FIGS. 1-5 show a first embodiment of a cannula of the invention. FIG. 1 shows a cannula in the first rotational position and FIG. 5 shows the cannula in the second rotational position. FIGS. 2-4 illustrate the course of movements between the first and the second rotational position. Cannula 1 for puncturing body cavities comprises an outer sleeve 2 having a longitudinal cut 6 and an inner sleeve 3 having a longitudinal cut 7 (cf. the sectional view in FIG. 1b). Each sleeve comprises a proximal end 5 and distal end 4. The inner sleeve 3 is arranged in the outer sleeve 2 so as to be longitudinally displaceable therein and may be rotated within the outer sleeve 2 such that the longitudinal cut 7 of the inner sleeve 3 is completely covered by the outer sleeve 2 in the first rotational position as shown in FIGS. 1a and 1b. FIG. 1b clearly shows that the two longitudinal cuts 6 and 7 of the outer and the inner sleeve are offset. In the shown position, the puncture tip 9 distally extends from the outer sleeve 2 at the distal end 4 of the inner sleeve 3. With this sharpened puncture tip 9 a body cavity, such as the bladder, can be punctured. The proximal end 5 of the cannula 1 according to the first embodiment is provided with two handle portions or wings 8a and 8b, which prevent the inner sleeve 3 from turning as long as the puncture tip 9 of the inner sleeve 3 distally extends from the outer sleeve.

So as to make it possible to rotate the two sleeves against each other so that the longitudinal cuts 6 and 7 of the two sleeves are placed on top of each other, as shown in FIGS. 5a and 5b, the inner sleeve 3 first has to be proximally retracted with respect to the outer sleeve 2. This can be achieved in that the first handle portion 8a, which is connected to the inner sleeve 3, is proximally shifted with respect to the second handle portion 8b, which is connected to the outer sleeve 2, as shown in FIGS. 2 and 3. In the position shown in FIG. 3a, the two handle portions or wings 8a and 8b do no longer block each other so that they may be rotated against each other (cf. FIGS. 4a and 4b). By rotating the two wings 8a and 8b against each other, the inner sleeve 3 is also rotated against the outer sleeve 2 (cf. FIG. 4b). In the second rotational position as shown in FIG. 5, the two sleeves 2 and 3 are rotated against each other to such an extent that their longitudinal cuts 6 and 7 are circumferentially aligned and are thus placed on top of each other. As shown in FIG. 5b, a catheter accommodated in the cannula may in this position be laterally (i.e. to the bottom in FIG. 5b) removed from the cannula.

Further details of the handle portions or wings are shown in the detailed views of FIGS. 6a-6f.

FIGS. 7-10 show the sequence of FIGS. 1-5 for a second preferred embodiment of the cannula of the invention. In this embodiment, the two wings 8a and 8b have been replaced by two handle portions or adjusting wheels 18a and 18b, which are connected to one another via a thread 10, such as a thread with a high pitch. Due to this thread structure, a rotation of the inner and outer sleeves against each other simultaneously and automatically results in a longitudinal shifting of the sleeves. Thus, the two movement portions that are necessary in the first embodiment are coupled in a single movement portion.

Figure 7A:
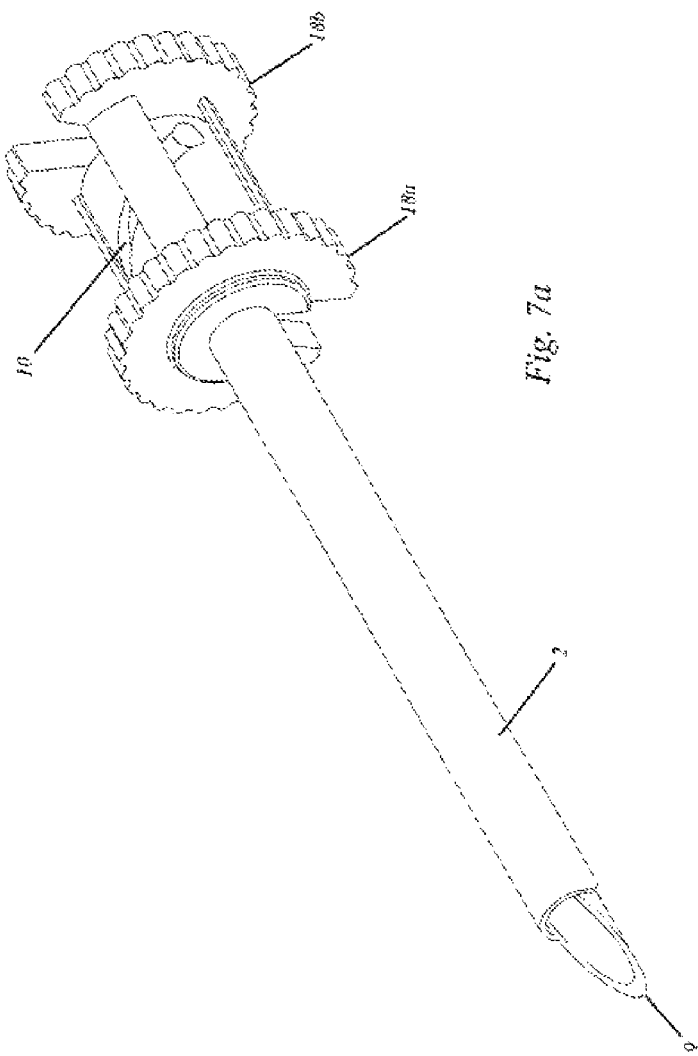
Figure 7B:
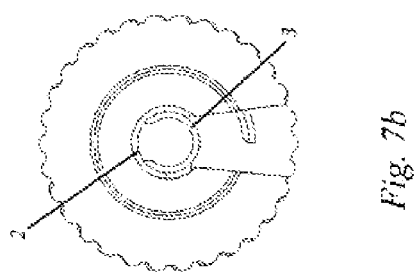
Figure 9A:
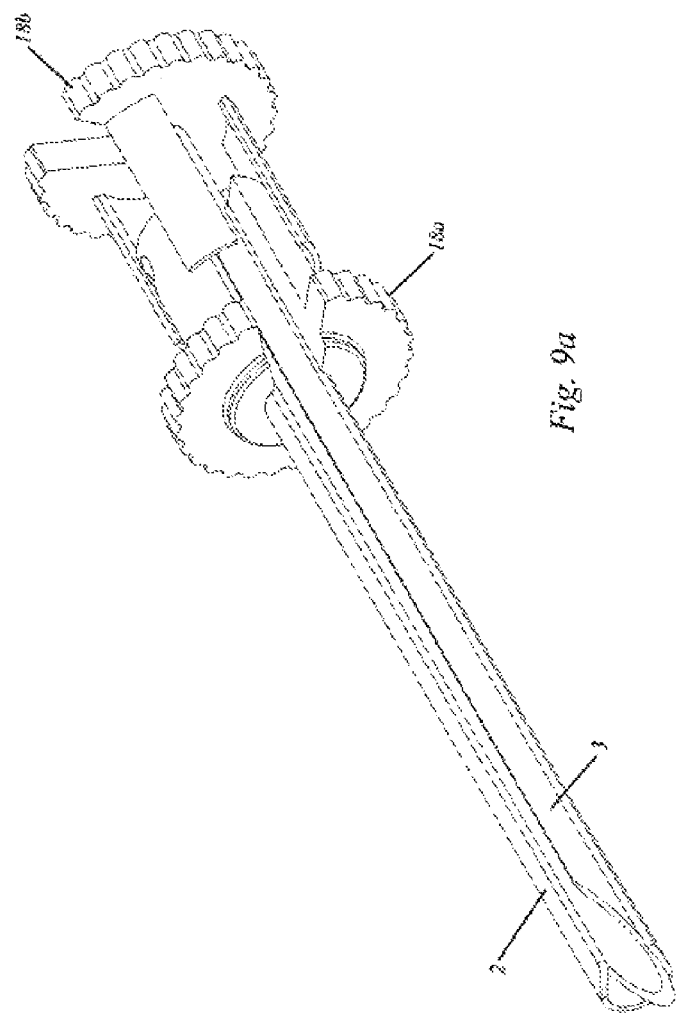
Figure 9B:
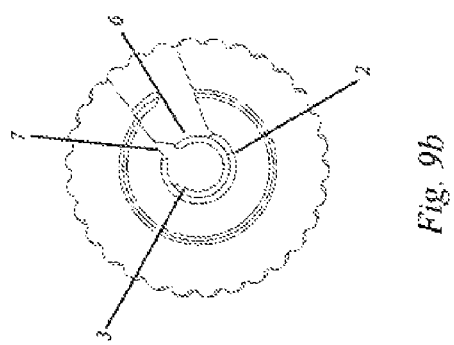
Figure 10A:
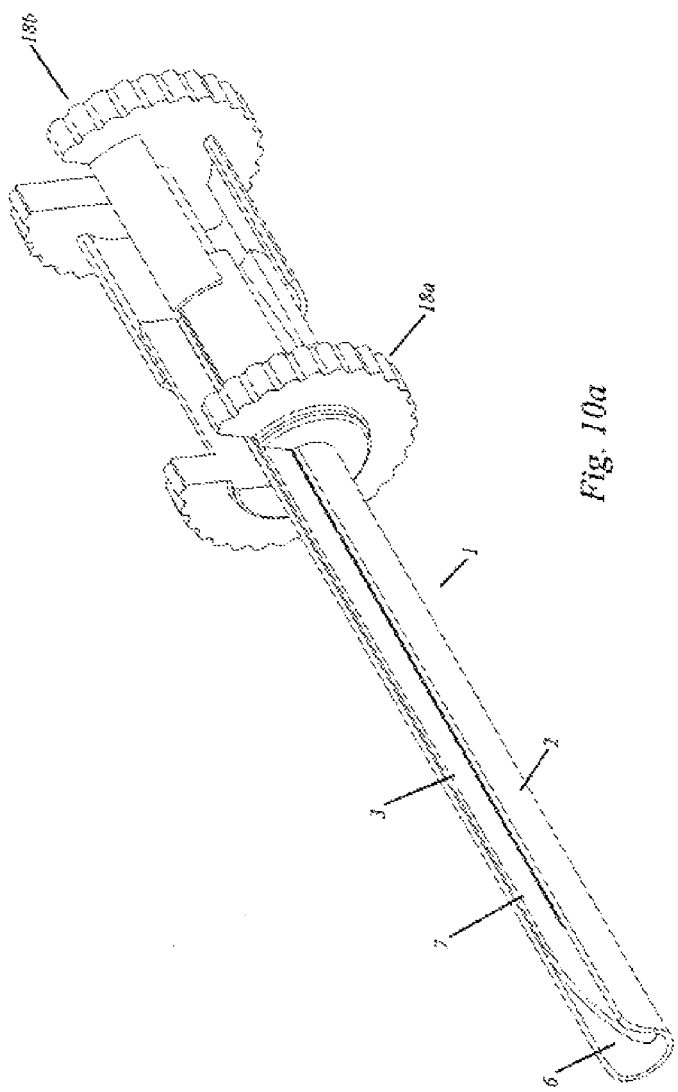

FIGS. 7a and 7b show the cannula of the second embodiment in the first rotational position, in which the longitudinal cut 7 of the inner sleeve 3 is completely covered by the outer sleeve 2 (cf. sectional view in FIG. 7b). If the two handle portions 18a and 18b are rotated against each other (cf. FIGS. 8 and 9), the inner sleeve 3 is not only rotated against the outer sleeve 2 in the same manner (cf. FIGS. 8b and 9b), but simultaneously the inner sleeve 3 is proximally retracted into the outer sleeve 2 (cf. FIGS. 8a and 9a). When the second rotational position is reached (cf. FIGS. 10a and 10b) so that the longitudinal cuts 6 and 7 of the two sleeves 2 and 3 are aligned or placed on top of each other, the puncture tip 9 of the inner sleeve 3 is simultaneously retracted into the outer sleeve 2 (cf. FIG. 10a) to such an extent that the puncture tip is covered and protected by the outer sleeve 2. In the second rotational position as shown in FIG. 10a, the operator is effectively protected from injury and infection.

Figure 10B:
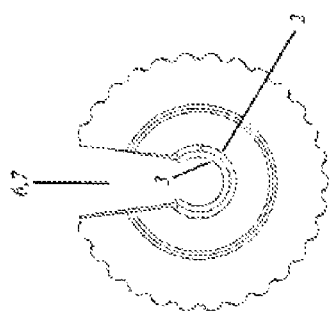
Figure 11A:
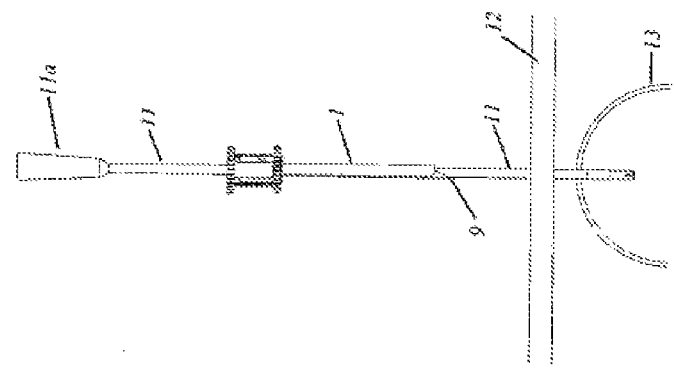
FIGS. 11a-11f show the functional principle of the cannula according to the invention.
Figure 11B:
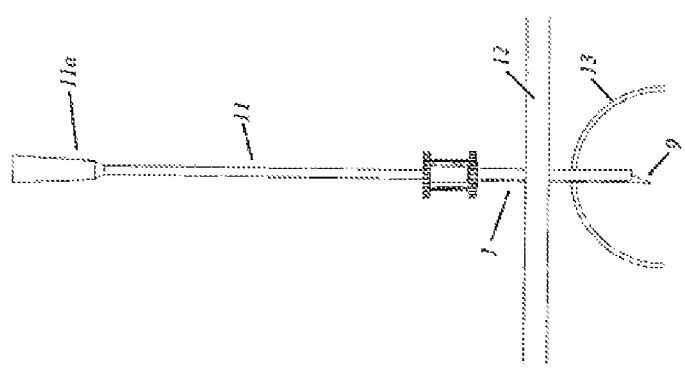
Figure 11C:
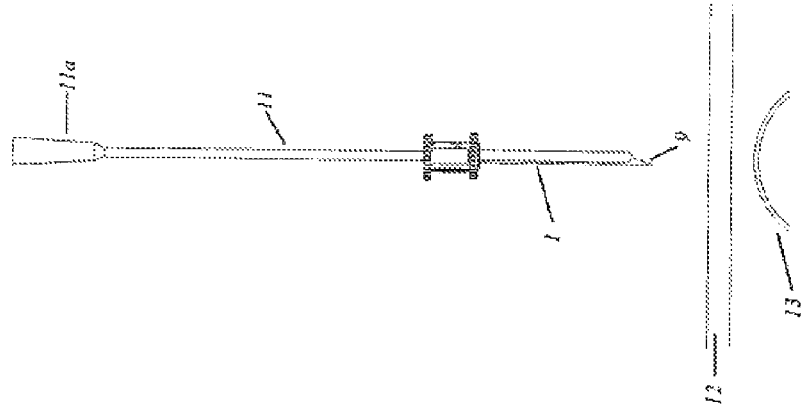
Figure 11F:
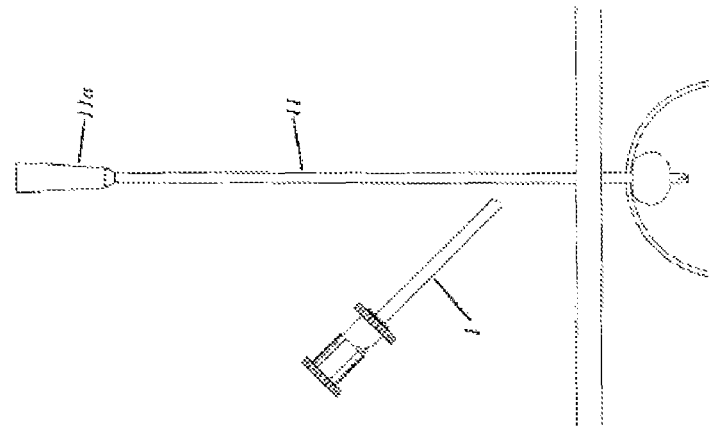
Figure 11E:
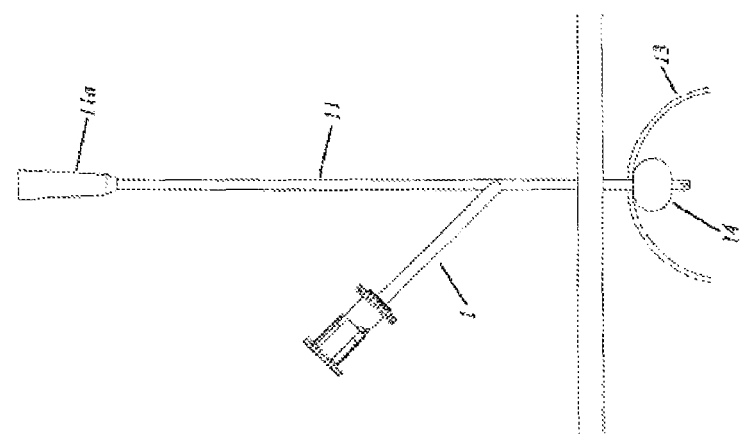
Figure 11D:
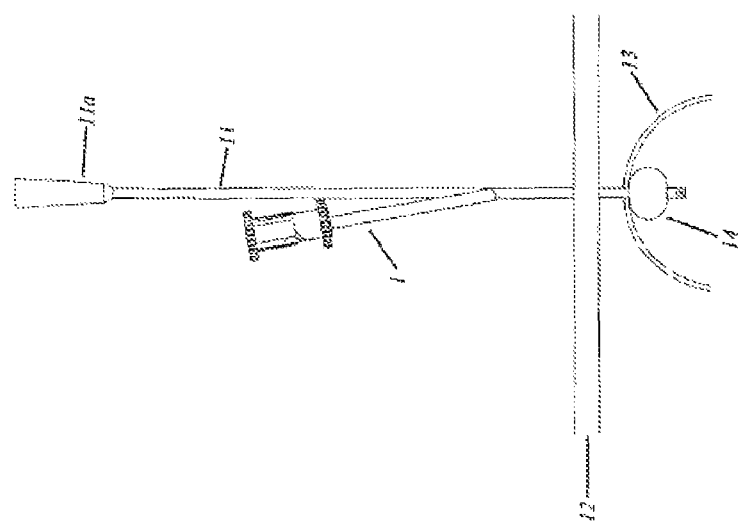

FIGS. 11a to 11f schematically show the mode of operation of the cannula according to the invention in more detail. Reference numeral 13 relates to a body cavity, such as a bladder, below a roughly sketched abdominal wall 12. In order to introduce the catheter 11 into the body cavity 13, it is inserted in a cannula 1 according to the invention, whereupon the cannula 1 is inserted together with the catheter 11 by means of the puncture tip 9 through the abdominal wall 12 into the body cavity 13 (cf. FIG. 11b). Upon puncturing, the cannula 1 is no longer needed and therefore retracted via the catheter 11 (cf. FIG. 11c). The neck 11a, however, prevents the cannula 11 from being completely removed from the cannula 1. Therefore, in the position shown in FIG. 11c, the two sleeves 2 and 3 of the cannula 11 are rotated against each other until their longitudinal cuts are placed on top of each other, as shown in FIGS. 10a and 10b. By rotating the sleeves against each other, the cannula tip or puncture tip 9 of the inner sleeve is simultaneously retracted into the outer sleeve, as described above. The catheter 11 can now be laterally removed through the two longitudinal cuts of the sleeves placed on top of each other or the cannula can be removed from the catheter (cf. FIGS. 11d-11f). Since the puncture tip 9 is completely covered or protected by the outer sleeve 2, damage to the catheter 11 or injury of the operator is not possible.

Figure 12D:
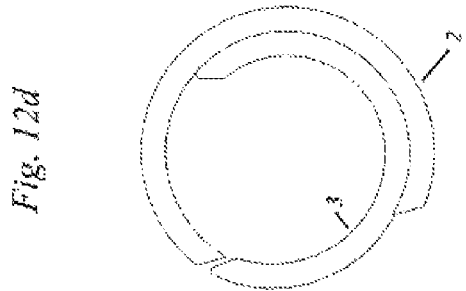
FIGS. 12a-12d show the mode of operation of the cannula sleeves according to a preferred embodiment.
Figure 12C:
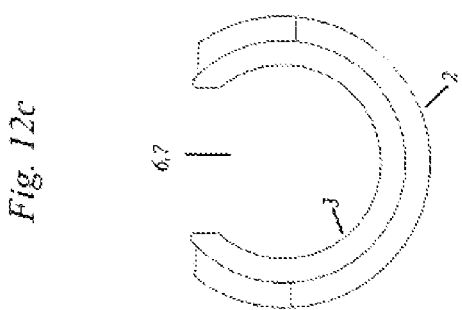
Figure 12B:
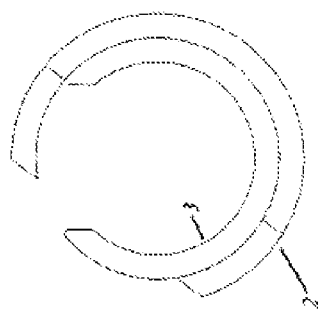
Figure 12A:
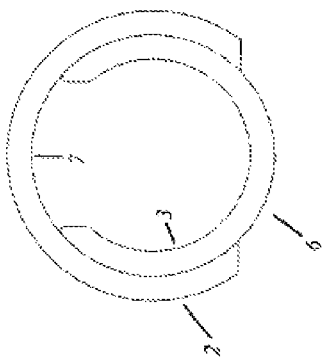

According to the invention, it is preferred that the inner and the outer sleeve and/or the two handle portions or wings interlock in the second position. Thus, it is made sure that the puncture tip 9 of the inner sleeve 3 is securely kept within the outer sleeve 2 when the cannula 1 is removed from the catheter 11 (cf. FIGS. 11d-11f). To this end, suitable retainers for locking or latching are preferably provided, such as, e.g., engagement hooks that cannot be easily disengaged. Disengageable locking or latching is preferred so that the cannula can only be used as a disposable cannula. Alternatively or in addition, the cannula can be configured such that the inner sleeve is prevented from completely turning back from the second position into the first position. This can for example be achieved in that the inner sleeve is prestressed within the outer sleeve. When the cannula is then opened by rotation of the two sleeves against each other (cf. FIGS. 12a-12c), the diameter of the inner sleeve is widened for being prestressed. The widened diameter of the inner sleeve then blocks a rotational movement when it is tried to completely rotate the inner sleeve 3 into the outer sleeve 2, as shown in FIG. 12d.

According to the invention, the sharp puncture tip is only provided at the inner sleeve, whereas the distal end of the outer sleeve is blunt and/or configured such that injuries caused at this distal end are avoided as far as possible. Thus, puncturing is made only by means of the inner sleeve, which is sharpened. In other words, the force necessary for puncturing is transferred from the puncture tip of the inner sleeve to the tissue. A stable storage of the inner sleeve is advantageous here. It is therefore preferred according to the invention that the distal end of the inner surface of the outer sleeve comprises two stabilising elements, which stabilise the inner sleeve during puncturing. Such a stabilisation can for example be achieved by means of two projections or protrusions 14, as shown in FIGS. 13a and 13b. These two projections 14, which are provided at the inner surface of the outer sleeve, serve during puncturing as locating points for the inner sleeve. Thus, the inner cannula is stabilised against any compressive or torsional forces during puncturing. The inner sleeve is thus prevented from springing back within the outer sleeve, which improves the operator's feeling during puncturing.

FIG. 14 shows a third embodiment of a cannula according to the invention comprising two handle portions 18a and 18b that are interconnected via a thread 10, such as a thread with a high pitch. Due to this thread structure, a rotation of the inner and the outer sleeve against each other simultaneously and automatically leads to a longitudinal shifting of the sleeves as in the second embodiment.

Figure 16A:
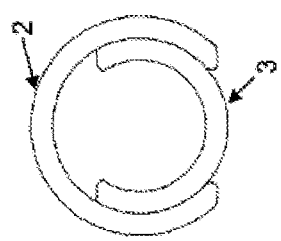
Figure 16B:
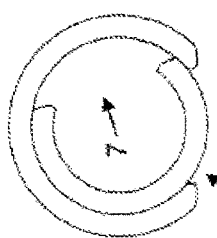
Figure 16C:
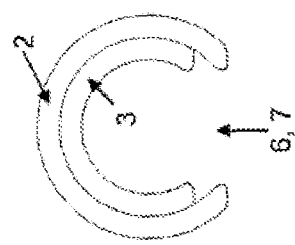
Figure 16D:
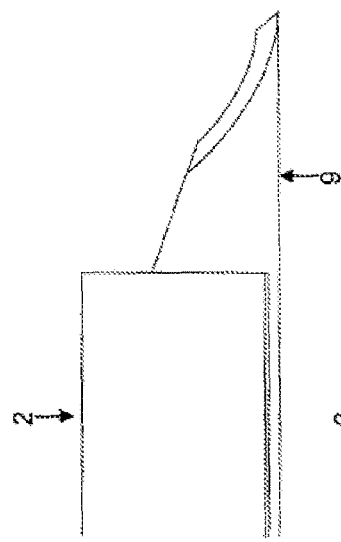
Figure 16E:
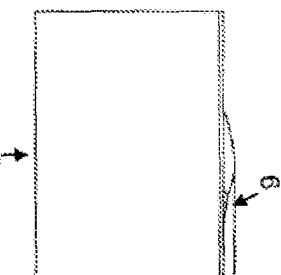
Figure 16F:
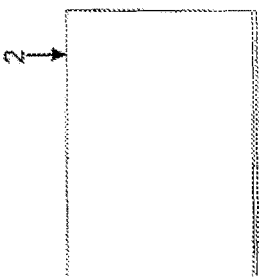

FIGS. 15a and 15b show the cannula of the third embodiment in the first rotational position, in which the longitudinal cut 7 of the inner sleeve 3 is completely covered by the outer sleeve 2 (cf. sectional view in FIGS. 15b and 16b). In this rotational position, for example puncturing is possible. If the two handle portions 18a and 18b are now rotated against each other (cf. FIGS. 15c and 15e), the inner sleeve 3 is not only rotated in the same manner against the outer sleeve 2 (cf. FIGS. 15d, 15f, 16d and 16f), but simultaneously the inner sleeve 3 is proximally retracted into the outer sleeve 2 (cf. FIGS. 16a, 16c and 16e). In the third rotational position as shown in FIGS. 15c, 15d, 16c and 16d, the puncture tip 9 of the inner sleeve 3 is already retracted so far into the outer sleeve 2 (cf. FIG. 16c) that the puncture tip is covered and protected by the outer sleeve 2. In the third rotational position shown in FIG. 15c, the operator is therefore effectively protected from injury and infection. If the second rotational position has been reached (cf. FIGS. 15e, 15f, 16e and 16f), the longitudinal cuts 6 and 7 of the two sleeves 2 and 3 are placed on top of each other, i.e. are aligned.

FIG. 17 shows the cannula according to the third embodiment before its mounting. It is therefore evident how the two handle portions 18a and 18b match and interact. FIGS. 18 and 18a show the cannula upon mounting, but before use, so that the handle portion 18a is inserted so far into the handle portion 18b that both portions are engaged. The cannula tip 9 is thus stored and protected within the outer sleeve 2. Only in the puncturing position, as shown in FIG. 19a, is the cannula tip exposed for puncturing. The two handle portions can for example be engaged by providing the first handle portion 18a with an engagement opening 10c (cf. FIG. 20d) with which a catch (not shown) within the second handle portion 18b engages. Thus, the cannula is located and retained in the situation shown in FIG. 18.

For transferring the cannula from the mounting position as shown in FIG. 18 into the puncturing position as shown in FIG. 19a, the operator has to distally shift or press the first handle portion 18a into the second handle portion 18b. The catch is thereby released from the engagement opening 10c, whereupon it proximally slides through the groove 10d before irreversibly engaging with the engagement opening 10b, because the engagement opening 10b is deeper than the groove 10d. Thus, the cannula tip is safely located as shown in FIG. 19a and cannot slide back into the sleeve 2 during puncturing.

If the inner sleeve 3 is retracted into the outer sleeve 2 together with the cannula tip 9 by twisting the two handle portions 18a and 18b (cf. FIGS. 19b-19d), the catch slides through the thread 10 (cf. FIGS. 20d and 20b) until reaching a further engagement opening 10a (cf. FIG. 20b) with which the catch engages so that the cannula is located or secured in the second rotational position. If necessary, further engagement positions may be provided; however, preferably, the handle portions and/or sleeves are interlocked at least in the first and second rotational positions.

FIGS. 21a-21c show a cannula according to a fourth embodiment of the present invention. In this embodiment, the handle portion 18a, which is connected to the inner sleeve 3, is configured as a pressure plate. With this pressure plate, the operator may, e.g., exert pressure over a large surface area during puncturing with his/her palm or thumb. This ensures easy puncturing for the operator and a safe mode of operation. Since, if necessary, the inner sleeve 3 should be capable of receiving a catheter 11, the pressure plate is preferably provided with a slot or guide 19 for a catheter 11 so as to prevent the catheter during puncturing, e.g., from getting wedged or jammed between the pressure plate and the palm or thumb. As shown in FIG. 21c, the catheter 11 is guided in a level movement within the plane of the pressure plate 18a to the centre of the latter by means of a plurality of catches in the guide 19, from where the catheter 11 extends into the inner sleeve 3.

The outer sleeve 2 and/or the handle portions 18a and/or 18b are preferably made of plastics. Suitable plastics materials are i.a. polyamides, polysulphones and high-performance plastics, such as, e.g., polyether ether ketone (PEEK). An outer plastics sleeve is a particularly effective protective means for the retracted cannula tip since such a plastics sleeve is hard to break and has not sharp edges at its distal end that could cause injuries.

It is particularly preferred to produce the outer sleeve 2 and the handle portion 18b connected to it of one piece of plastics. This makes production easy and cost-effective. Such an embodiment is exemplarily shown in FIGS. 22a-22f. Here, the outer sleeve 2 and the handle portion 18b are configured such that they can be (injection) moulded from plastics in a simple and cost-effective manner. The catch within the handle portion 18b, which is not shown, can thus also easily be manufactured. The safety cannula according to the present invention reduces the risk of injury and infection during use as compared to conventional puncturing cannulae, in particular splittable cannulae. The safety cannula according to the present invention can be produced at low cost and is simple to use. The safety mechanism is an automatic mechanism and does not require any specific staff training. Moreover, the concept of the present safety cannula is variable in use and may particularly be used with different puncturing cannulae and different catheters.

The invention claimed is:

1. A suprapubic cannula for puncturing body cavities comprising
   outer and inner longitudinally cut sleeves each sleeve having a proximal end, a distal end, and a handle portion at the proximal end, each handle portion including flange,
   wherein the inner sleeve is arranged within the outer sleeve to be longitudinally displaceable and rotatable within the outer sleeve such that the longitudinal cut of the inner sleeve is covered in a first rotational position by the outer sleeve and the longitudinal cuts of the inner sleeve and the outer sleeve are placed on top of each other in a second rotational position,
   wherein the inner sleeve is provided at its distal end with a puncture tip, the inner sleeve having an extended position corresponding to the first rotational position, in which the puncture tip extends outside the distal end of the outer sleeve, and a retracted position corresponding to the second rotational position, in which the puncture tip is completely retracted into the outer sleeve; and
   wherein the handle portions interlock through a threaded engagement at a location that is between the flanges, the threaded engagement drives movement of the inner sleeve between the extended and first rotational position and the retracted and second rotational position in response to rotation of the handle portion relative to each other.

2. The cannula of claim 1, wherein the inner and the outer sleeves and/or the handle portions are non-detachably interlocked in the second rotational position.

3. The cannula of claim 1, wherein the handle portions include a first handle portion connected to the inner sleeve and a second handle portion connected to the outer sleeve, wherein the second handle portion is located between the first handle portion and the distal end of the outer sleeve.

4. The cannula of claim 3, wherein the first handle portion includes a pressure plate.

5. The cannula of claim 1, wherein the distal end of the outer sleeve is blunt.

6. The cannula of claim 1, configured in that the inner sleeve is prevented from completely turning from the second rotational position back into the first rotational position.

7. The cannula of claim 1, wherein the distal end of an inner surface of the outer sleeve is provided with two stabilizing elements which stabilize the inner sleeve during puncturing.

8. The cannula of claim 1, wherein rotation of the inner sleeve relative to the outer sleeve from the first rotational position to the second rotational position drives the inner sleeve from the extended position to the retracted position via the threaded engagement.

9. The cannula of claim 1, wherein the handle portions interlock in the second rotational and retracted position using a latch.

10. The cannula of claim 1, wherein rotation of the inner sleeve from the second rotational position to the first rotational position is blocked by the outer sleeve.

11. The cannula of claim 1, wherein the longitudinal cut of the inner sleeve is placed substantially opposite of the longitudinal cut of the outer sleeve in the first rotational position.

12. A kit comprising a cannula according to claim 1 and a catheter that is receivable in the inner sleeve of the cannula, wherein the catheter is removable from the cannula in the second rotational position of the cannula by the longitudinal cuts of the inner and outer sleeves placed on top of each other.

* * * * *